(12) United States Patent
Kroker et al.

(10) Patent No.: US 6,350,352 B2
(45) Date of Patent: *Feb. 26, 2002

(54) PROCESS FOR SEPARATING BY DISTILLATION PURE (METH)ACRYLIC ACID FROM MIXTURES

(75) Inventors: Ruprecht Kroker, Bobenheim-Roxheim; Manfred Wiedemann, Ludwigshafen, both of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,706

(22) PCT Filed: Aug. 26, 1997

(86) PCT No.: PCT/EP97/04639

§ 371 Date: Feb. 22, 1999

§ 102(e) Date: Feb. 22, 1999

(87) PCT Pub. No.: WO98/08798

PCT Pub. Date: Mar. 5, 1998

(30) Foreign Application Priority Data

Aug. 27, 1996 (DE) .......................... 196 34 614

(51) Int. Cl.$^7$ .............................. B01D 3/34; B01D 3/28; C07C 51/44

(52) U.S. Cl. ............... 203/6; 203/72; 203/78; 203/80; 203/89; 203/8; 203/40; 203/DIG. 21; 562/600

(58) Field of Search ............... 203/8–9, 2, 100, 203/40, 89, 80, 91, DIG. 21, 72, 78; 202/197, 205; 562/600

(56) References Cited

U.S. PATENT DOCUMENTS

| | | | | | |
|---|---|---|---|---|---|
| 3,442,766 | A | * | 5/1969 | Smith et al. | 202/197 |
| 4,110,370 | A | * | 8/1978 | Engelbach et al. | 203/49 |
| 4,417,951 | A | * | 11/1983 | Stanisic et al. | 203/40 |
| 4,877,487 | A | * | 10/1989 | Lloyd | 202/181 |
| 5,425,849 | A | * | 6/1995 | Feres | 159/13.1 |

\* cited by examiner

Primary Examiner—Virginia Manoharan
(74) Attorney, Agent, or Firm—Oblon, Spivak, McClelland, Maier & Neustadt, P.C.

(57) ABSTRACT

A process for distillative separation of pure (meth)acrylic acid from mixtures which include comprise (meth)acrylic acid and dimers and oligomers of (meth)acrylic acid and are essentially free from aldehydes and from components whose boiling point is lower than that of (meth)acrylic acid, using a distillation apparatus which has a thin-film evaporator, a condenser and a connection which contains a baffle device and links the thin-film evaporator and the condenser.

11 Claims, 1 Drawing Sheet

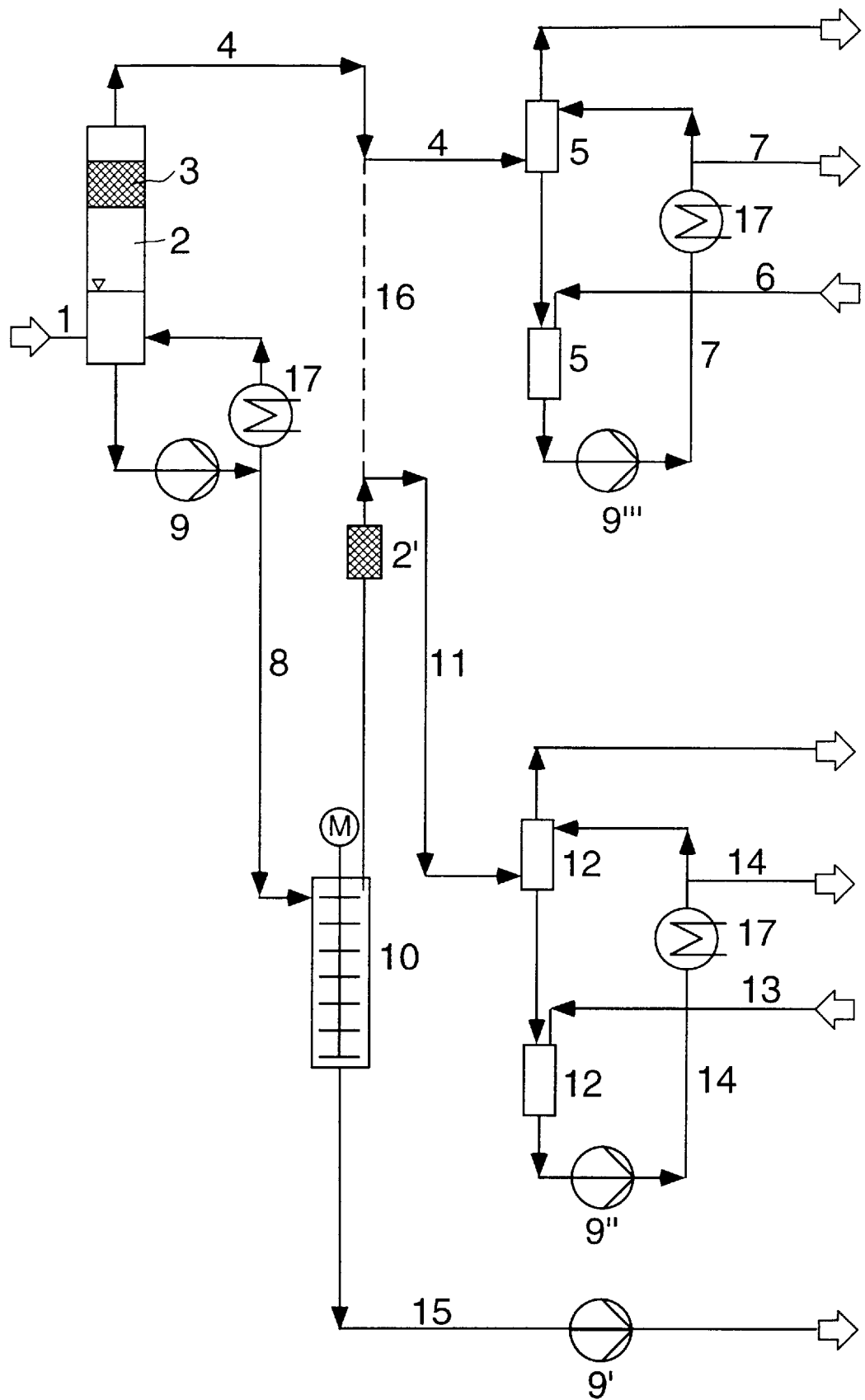

PROCESS FOR SEPARATING BY DISTILLATION PURE (METH)ACRYLIC ACID FROM MIXTURES

BACKGROUND OF THE INVENTION

1. Field of the Invention

The present invention relates to a process for distillative separation of pure (meth)acrylic acid from mixtures which comprise (meth)acrylic acid and dimers and oligomers of (meth)acrylic acid and are essentially free from aldehydes and other components whose boiling point is lower than that of (meth)acrylic acid.

2. Description of the Background (Meth)acrylic acid is used as an abbreviated written form and denotes acrylic acid or methacrylic acid. (Meth)acrylic acid, either per se or in the form of its esters, is particularly important in the preparation of polymers for a very wide variety of applications, for example as an adhesive, and especially in the liquid aggregate state has a high propensity to polymerize. Safe storage of essentially pure liquid (meth) acrylic acid is possible even at low temperatures only with the addition of polymerization inhibitor.

(Meth)acrylic acid is obtainable inter alia by catalytic gas phase oxidation of alkanes, alkanols, alkenes or alkenals having 3 or 4 C atoms. (Meth)acrylic acid is obtainable with particular advantage, for example, by catalytic gas phase oxidation of propene, acrolein, tert-butanol, isobutene, isobutane, isobutyraldehyde or methacrolein.

When considering possible starting compounds, however, one should not ignore those from which the actual $C_3/C_4$ starting compound is formed only during the gas phase oxidation, as an intermediate. An example which may be mentioned is the methyl ether of tert-butanol.

In the reaction these starting gases, generally diluted with inert gases such as nitrogen, $CO_2$, saturated hydrocarbons and/or steam, are passed in the form of a mixture with oxygen and at elevated temperatures (usually from 200 to 400° C.) at atmospheric or superatmospheric pressure over transition metal (containing Mo, V, W and/or Fe, for example) mixed-oxide catalysts and are converted by oxidation to (meth)acrylic acid (cf. e.g. DE-A 44 05 059, EP-A 253 409, EP-A 92 097, DE-A 44 31 949).

Because of the numerous parallel and follow-on reactions that occur in the course of the catalytic gas phase oxidation, and because of the inert diluting gases that are used, the catalytic gas phase oxidation produces not pure (meth) acrylic acid but instead a reaction mixture which essentially comprises (meth)acrylic acid, the inert dilution gases and byproducts and from which it is necessary to separate the (meth)acrylic acid.

(Meth)acrylic acid is usually separated from the reaction mixture by way of extractive and distillative separation techniques. In such techniques, the (meth)acrylic acid formed is typically first of all absorbed from the gas phase oxidation reaction mixture into a suitable absorbent. Subsequent distillative separation of the absorbate customarily gives a crude (meth)acrylic acid which, on traversing further distillative separation stages, frequently produces a pure (meth)acrylic acid (cf. e.g. DE-A 44 36 243, DE-C 21 36 396, DE-A 43 08 087, EP-A 297 445, EP-A 117 146, EP-B 102 642, GB-B 1 346 737 and DE-C 22 07 184).

A feature of all of these rectificative separation techniques, irrespective of whether the (meth)acrylic acid is separated off at the top or at the bottom and even when polymerization inhibitors are used, is that after a relatively short time during the rectificative separation a deposit is formed within the rectification devices, as a result of which rectification, which is normally carried out continuously, must be interrupted at intervals to allow removal of the deposit formed.

In recent times extensive investigations have been carried out into how to reduce the problem of the formation of deposits during the distillative separation of (meth)acrylic acid from the reaction mixtures or product mixtures obtained in the preparation of (meth)acrylic acid.

For instance, DE 195 01 326.3 describes a method of rectificative is separation of (meth)acrylic acid from a mixture comprising (meth)acrylic acid as principal constituent and lower aldehydes as secondary constituents in a rectification column which consists of a stripping section and a rectifier section, where the starting mixture comprising the (meth)acrylic acid that is to be separated by rectification is not supplied directly to the rectification column but instead is first of all passed into a heated dwell vessel, connected on the vapor side with the rectifier section of the rectification column, in which vessel the starting mixture is held at boiling, and instead of the starting mixture per se the bottom liquid from the residence vessel is supplied to the rectification column. In this method, the mixture is processed to generally liquid mixtures with a (meth)acrylic acid content of from 5 to 25% by weight, as are generally obtained following the addition of an absorbent to the reaction mixture obtained from the catalytic gas phase oxidation, and after subsequent desorption, as the outgoing flow from the desorption column. In addition to (meth)acrylic acid, these mixtures still comprise large amounts of absorbent and lower aldehydes as secondary components.

A more recent process for the continuous distillative separation of liquid mixtures whose principal constituent is (meth)acrylic acid is described in DE 195 39 295.7, which is also directed mainly toward the problem of reducing the formation of deposits during rectification. According to this application, the distillative separation of a mixture which in general has a content of (meth)acrylic acid of $\geq 95\%$ by weight (crude (meth)acrylic acid) is conducted in a distillation device which has a distillation still, a condenser and a connection between distillation still and condenser, and to which the liquid mixture that is to be separated is supplied continuously, wherein a fraction of the distillation still liquid is withdrawn in superheated form and is passed back under pressure release into the distillation device in the course of this process.

All of the processes described in the prior art have the common feature that the bottom product of the distillations or rectifications, which contains up to 99% by weight (meth)acrylic acid as the target substance, is not likewise subjected to distillative workup. The resulting bottom product, which contains a relatively high proportion of (meth)acrylic acid in the form of oligomers, has to date been used as a component in a coupled production process for butyl (meth)acrylate. Coupled production of this kind is, however, not always possible or economic.

SUMMMARY OF THE INVENTION

It is an object of the present invention, accordingly, to provide a process which is able to isolate pure (meth)acrylic acid, as simply as possible and with a high yield, from the (meth)acrylic acid which is present in the bottom product. A further object, to be achieved with the aid of this process, is to produce not only as much pure (meth)acrylic acid as possible but at the same time to produce a correspondingly small amount of residue requiring landfill or incineration.

We have found, in the course of the investigations leading to this invention, that this object is achieved, surprisingly, by a simple distillation process.

The present invention accordingly provides a process for distillative separation of pure (meth)acrylic acid from mixtures which comprise (meth)acrylic acid and dimers and oligomers of (meth)acrylic acid and are essentially free from aldehydes and from components whose boiling point is lower than that of (meth)acrylic acid, such as water and acetic acid, for example, using a distillation apparatus which has a thin-film evaporator, a condenser, and a connection which contains a baffle device and links the thin-film evaporator and the condenser.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

The sole Figure depicts a diagram for practicing the present process.

DETAILED DESCRIPTION OF THE PREFERRED EMBODIMENTS

The term crude (meth)acrylic acid as used in the present application refers to a (meth)acrylic acid which in general has a purity of ≧95% by weight, frequently ≧97% by weight, the impurities being drawn in particular from lower aldehydes (for example formaldehyde, acetaldehyde, acrolein, methacrolein, propionaldehyde, n-butyraldehyde, benzaldehyde, furfural or crotonaldehyde), water, lower alkanecarboxylic acids (for example acetic and propionic acid) and anhydrides of alkanecarboxylic acids (for example maleic anhydride).

The term pure (meth)acrylic acid as used in this application refers to a (meth)acrylic acid whose purity is ≧98% by weight, frequently ≧99% by weight.

The term residue (meth)acrylic acid as used in this application refers to the residual (meth)acrylic acid which remains in the bottom product obtained in the distillative preparation of pure (meth)acrylic acid.

The mixture which is to be treated here generally has a content of residue (meth)acrylic acid of not more than approximately 99% by weight, the content generally being from approximately 20 to approximately 99% by weight, preferably from approximately 70 to approximately 95% by weight.

The content of dimers and oligomers of (meth)acrylic acid is generally not more than approximately 5000 ppm, preferably not more than approximately 1000 ppm, and increases with the duration and/or temperature of storage.

As further components, the mixture comprises processing stabilizers which inhibit the polymerization of (meth)acrylic acid, examples being air, hydroquinone, hydroquinone monomethyl ether, p-nitrosophenol, p-methoxy-phenol or phenothiazine, or mixtures of two or more thereof, preference being given to the use of phenothiazine, in an amount from approximately 50 to approximately 1000 ppm.

The amount of the processing stabilizer (polymerization inhibitor) based on the (meth)acrylic acid (by weight) is normally from approximately 200 to approximately 800 ppm.

Because of the inhibiting effect that atmospheric oxygen has on the polymerization of (meth)acrylic acid it is advantageous to operate the distillation apparatus that is used in accordance with the invention with a throughflow of air.

The mixture also includes aldehyde-aminoguanidine adducts and/or aldehyde-hydrazine adducts in an amount of up to approximately 2000 ppm which originate from the aminoguanidine hydrocarbonate and/or hydrazine (derivatives) added at the beginning of the workup of the reaction mixture obtained in the gas phase oxidation.

The term "essentially free from" used in connection with the present invention means that the content of the aldehydes and of the "further components", to which reference is made in this context, especially of the aldehydes and/or low-boiling components, for example water and lower alkanecarboxylic acids, is in each case not more than approximately 1000 ppm, preferably approximately 500 ppm and, in particular, approximately 300 ppm.

The novel process is employed with particular advantage in connection with the workup of a bottom product, containing residual (meth)acrylic acid, that is obtained in the distillative preparation of pure (meth)acrylic acid.

For the purposes of the novel process it is essential that the distillation apparatus is designed as a thin-film evaporator (Sambay or Luva evaporator) which can of course be configured in one or more stages. The thin-film evaporator configuration is essential for the advantageous implementation of the process in so far as with other evaporators, for example tube evaporators, it is difficult to work up the in most cases relatively viscous mixtures that are to be worked up in this case, which generally have a viscosity of from approximately 50 to approximately 1000 mPas at 50° C., and formation of deposits or encrustation of the apparatus is observed after only a relatively short time. Thin-film evaporators that can be used for the purposes of the present invention, in addition to those mentioned above, are falling film evaporators and filmtruders.

In addition, the apparatus to be used in accordance with the invention has a connection which has a baffle device and links the thin-film evaporator and the condenser. Apart from the baffle device, which prevents the entrainment of liquid droplets, especially of the polymerization inhibitor, the connection is essentially free from further internals. Possible baffle devices that can be used are demistors, i.e. wire mesh packings with a very large internal surface area, which can be fabricated, for example, from chromium nickel steels, aluminum, copper, nickel, polypropylene, polytetrafluoroethylene and so on, and a simple packing of Raschig rings etc.

To minimize the temperatures during workup the distillative separation of (meth)acrylic acid in accordance with the invention preferably takes place under reduced pressure. In this context it is judicious, in accordance with the invention, to operate under a pressure $\leqq 5 \times 10^4$ Pa, preferably at from approximately 0.1 to approximately $5 \times 10^4$ Pa, more preferably at from approximately 0.1 to approximately $3 \times 10^4$ Pa and, in particular, at approximately $7 \times 10^3$ Pa. The interior of the thin-film evaporator is generally at from approximately 40 to approximately 140° C., preferably from approximately 40 to approximately 100° C. and, in particular, at approximately 70° C., while the corresponding wall temperature of the thinfilm evaporator is from approximately 30 to 40° C. higher.

With preference, the above-described novel process for distillative separation of pure (meth)acrylic acid is coupled with the customary processes for obtaining pure (meth)acrylic acid from reaction mixtures obtained in connection with the preparation of (meth)acrylic acid, as mentioned at the outset when discussing the prior art.

Accordingly, the present invention additionally provides a process for distillative recovery of pure (meth)acrylic acid, comprising the following stages (a) and (b):

(a) separation by way of extractive and distillative separation techniques of pure (meth)acrylic acid from reaction mixtures obtained in connection with the preparation of (meth)acrylic acid, and (b) treatment of a bottom product, obtained in step (a) in a distillative separation technique and comprising (meth)acrylic acid, by a process for distillative separation of pure (meth)acrylic acid from mixtures, as defined above.

Pure (meth)acrylic acid is obtained both in step (a) and in step (b) in each case at the top, or laterally (step (a)) and at the top (step (b)).

In this connection, the product streams obtained in steps (a) and (b), comprising pure (meth)acrylic acid, can be combined.

In general, a storage stabilizer such as hydroquinone monomethyl ether is added to the pure (meth)acrylic acid obtained as product.

In a particularly preferred embodiment of the present invention step (a) is conducted as follows:

First of all a crude (meth)acrylic acid is obtained by a prior art process as described, for example, in EP 95 118 901 (EP-A 717 029).

The distillative preparation of pure (meth)acrylic acid in accordance with step (a) is then carried out by means of a single-stage distillation in which pure (meth)acrylic acid is taken off at the top in a distillation apparatus which has a distillation device, a condenser and a connection between the distillation device and the condenser and to which the liquid mixture that is to be separated, comprising crude (meth)acrylic acid, is supplied continuously, wherein at least part of the energy required to evaporate the liquid mixture is supplied to the distillation apparatus by continuously withdrawing from the distillation device a fraction of its liquid contents which are at a pressure $P_x$, heating this fraction to a temperature $T_y$, at a pressure $P_y$ which is above $P_x$, with the proviso that $T_y$, is above the boiling temperature $T_x$ of the liquid contents of the distillation device when subject to the pressure $P_x$ and is below the boiling temperature $T_y$ of the liquid contents of the distillation device when subject to the pressure $P_y$, and passing the liquid fraction withdrawn from the distillation device and superheated in this manner, relative to the pressure $P_x$, back to the distillation apparatus. A process of this kind is described in DE 195 39 295.7.

The mixture which remains as the bottom product in this process can then be passed directly into the second apparatus, for example by way of pumps, and can be worked up appropriately, as described above, as step (b).

A diagram of this process is shown in FIG. 1.

In this diagram the crude (meth)acrylic acid recovered from the extraction, which has been treated with aminoguanidine hydrogencarbonate (AGHC) and/or hydrazine to break down the aldehydes and contains polymerization inhibitors and a wetting agent, for example dodecylbenzenesulfonic acid, as antifouling agent is introduced via line (1) into a distillation unit (2) provided if desired with a demistor (3), and is distilled, the pure (meth)acrylic acid being taken off at the top and condensed by means of the line (4) in a cooling circuit (5), and being provided via feed line (6) with a stabilizer. The stabilized pure product thus obtained is transferred to a vessel (not shown) by way of the line (7), which (as shown) can be provided with a circulation pump (9''').

The bottom product obtained in the distillation in unit (2), containing residual (meth)acrylic acid, is drawn off and transferred via a feed line (8), which can if desired be provided with a circulation pump (9), into the thin-film evaporator (10), which is provided with a demistor (2+), where it is subjected to a residue distillation procedure. Pure (meth)acrylic acid is again taken off from the top and passed via the feed line (11) to a further cooling circuit where it is likewise treated with a stabilizer via the supply line (13). The pure product thus obtained is transferred into a vessel (not shown here) via the line (14), which (as shown) can be provided with a circulation pump (9''). The residue in the thin-film evaporator, which contains high-boiling compounds, is removed continuously from the thin-film evaporator via the discharge line (15), which contains a discharge pump (9'), and is passed on for incineration. The amount of residue produced, based on the initial amount of crude (meth)acrylic acid, is about 1–2% by weight.

As likewise shown diagrammatically in FIG. 1 by the dashed line (16), the pure (meth)acrylic acid taken off at the top in the residue distillation procedure can also be combined with the distillation product stream from the unit (2), which likewise consists of pure (meth)acrylic acid, by way of a connection incorporating a cooling device (16), and both product streams can be condensed together, provided with a storage stabilizer and transferred to a vessel which is not shown here.

It is also possible—as is shown likewise—for there to be circulation evaporators (17) at various points in the process.

Overall it should be borne in mind that the novel process can be carried out, preferably, continuously, but also discontinuously, and can in fact be conducted either alone or coupled with other process stages within a process preparing pure (meth)acrylic acid by gas phase oxidation with subsequent purification.

EXAMPLE

A bottom product of the following composition:

92% by weight of acrylic acid 4000 ppm of phenothiazine (process polymerization inhibitor)

2% by weight of dimers and oligomers of acrylic acid

2% by weight of adducts of AGHC and aldehydes/maleic anhydride

3% by weight of dodecylbenzenesulfonic acid (antifouling agent)

300 ppm of propionic acid 300 ppm of acetic acid 100 ppm of water, which was obtained in connection with a preparation by catalytic gas phase oxidation of acrolein and subsequent extractive and distillative purification thereof, was supplied to a distillation apparatus with a thin-film evaporator and a baffle device.

The precise data for the distillation apparatus and the mode of operation were as follows:

thin-film evaporator of the Sambay type with a wall area of 10 m² demistor with a diameter of 700 mm and a length of 1 m direct feed of the mixture to be separated into the thin-film evaporator with an entry temperature of from 30 to 90° C. at a rate of 0.5 m³/h;

pressure in the apparatus: $7 \times 10^3$ Pa (70 mbar);

boiling temperature at the top of the device: approximately 70° C.;

cooling circuit 80 m³/h.

In the condenser a condensate was obtained which comprised 99.7% by weight of acrylic acid and also less than 1000 ppm of diacrylic acid, about 300 ppm of propionic acid, about 300 ppm of acetic acid, <10 ppm of low molecular mass aldehydes and <1 ppm of phenothiazine and to which 200 ppm of hydroquinone monomethyl ether as storage stabilizer were added directly.

The yield of acrylic acid based on the amount introduced was approximately 90%. The bottom product, which was obtained in this distillation in an amount of approximately 10% based on the overall amount employed, consisted essentially of dimers and oligomers of acrylic acid, process stabilizer, antifouling agent, the adducts of AGHC and aldehydes/maleic anhydride, and a small amount of acrylic acid.

We claim:

1. A process comprising separating by distillative separation of purified (meth)acrylic acid from a mixture which comprise (meth)acrylic acid and dimers and oligomers of (meth)acrylic acid and are essentially free from aldehydes and from components whose boiling point is lower than that of (meth)acrylic acid, using a distillation apparatus which has a thin-film evaporator, a condenser and a connection which contains a baffle device and links the thin-film evaporator and the condenser, wherein said mixture is a bottom product obtained in a distillative preparation of purified (meth)acrylic acid, counting residual (meth)acrylic acid.

2. The process as claimed in claim 1, where a proportion of residual (meth)acrylic acid in said mixture is up to 99% by weight.

3. The process as claimed in claim 1, wherein said mixture comprises, as a polymerization inhibitor, phenothiazine, hydroquinone, hydroquinone monomethyl ether, p-nitrosophenol, p-methoxyphenol or mixtures of two or more thereof.

4. The process as claimed in claim 1, wherein the pressure in the thin-film evaporator is from $1 \times 10^3$ to $3 \times 10^4$ Pa.

5. The process as claimed in claim 1, wherein the temperature at the top of the thin-film evaporator during distillation is from 40 to 140° C.

6. The process as claimed in claim 1, wherein a storage stabilizer is added to the purified (meth)acrylic acid obtained as a product.

7. The process of claim 1, wherein said (meth)acrylic acid comprises 20–99% by weight (meth)acrylic acid and less than approximately 5,000 ppm of dimers and oligomers of (meth)acrylic acid.

8. The process of claim 1, wherein said essentially free from aldehydes mixture comprises $\leq 1,000$ ppm of aldehydes.

9. A process for distillative recovery of purified (meth)acrylic acid, comprising the following stages (a) and (b):

(a) separating by extractive and distillative separation techniques purified (meth)acrylic acid from reaction mixtures obtained in connection with preparation of (meth)acrylic acid, and (b) treating a bottom product, obtained in stage (a) in a distillative separation technique and comprising (meth)acrylic acid, and dimers and oligomers of (meth)acrylic acid and are essentially free from aldehydes and from components whose boiling point is lower than that of (meth)acrylic acid, using a distillation apparatus which has a thin-film evaporator, a condenser and a connection which contains a baffle device and links the thin-film evaporator and the condenser.

10. The process as claimed in claim 9, where the separation of purified (meth)acrylic acid in accordance with stage (a) is conducted in a distillation apparatus which has a distillation device, a condenser and a connection between the distillation device and the condenser and to which a liquid mixture that is to be separated is supplied continuously, where at least part of the energy required to evaporate said liquid mixture is supplied to the distillation apparatus by continuously withdrawing from the distillation device a fraction of its liquid contents which are at a pressure $P_x$, heating this fraction to a temperature $T_y$, at a pressure $P_y$ which is above $P_x$, with the proviso that $T_y$, is above the boiling temperature $T_x$ of the liquid contents of the distillation device when subject to the pressure $P_x$ and is below the boiling temperature $T_y$ of the liquid contents of the distillation device when subject to the pressure $P_y$, and passing the liquid fraction withdrawn from the distillation device and superheated, relative to the pressure $P_x$, back to the distillation apparatus.

11. The process as claimed in claim 9 where product streamers of purified (meth)acrylic acid obtained in stages (a) and (b) are combined.

* * * * *